United States Patent [19]

Wiles et al.

[11] Patent Number: 4,761,676
[45] Date of Patent: Aug. 2, 1988

[54] FAULT DETECTION AND RESET IN SURFACE REFLECTANCE METER

[75] Inventors: Gregory R. Wiles, Royal Oak; Robert J. Matzoll, Jr., Rochester Hills, both of Mich.

[73] Assignee: ATI Systems Inc., Madison Heights, Mich.

[21] Appl. No.: 899,467

[22] Filed: Aug. 22, 1986

[51] Int. Cl.⁴ .................. G01N 21/55; G01N 21/01; G04G 11/00; G04F 13/00
[52] U.S. Cl. ................................. 356/445; 356/447; 364/525; 364/569
[58] Field of Search ............... 364/525, 524, 569, 557, 364/556, 565; 250/559; 356/447, 446, 445; 350/273, 274, 275

[56] References Cited

U.S. PATENT DOCUMENTS 4,569,717 2/1986 Ohgami et al. ..................... 250/559

Primary Examiner—Parshotam S. Lall
Assistant Examiner—Steven A. Melnick
Attorney, Agent, or Firm—Krass & Young

[57] ABSTRACT

In a surface reflectance meter for directing light to a surface, receiving light reflected from the surface and measuring the rate of change of light flux upon withdrawal of a light chopper from the optical path, a fault detection means which detects and indicates a fault in the flux rate of change measurement is disclosed. In the preferred embodiment the rate of change of flux is detected by measuring the time for the light intensity to increase from a first to a second predetermined intensity and the fault detector means detects and indicates a fault when the light intensity does not reach the second predetermined intensity within a predetermined period of time. The surface reflectance meter is reset for repetition of the measurement upon indication of a fault. This invention is useful in portable surface reflectance meters which must be hand held to the surface to be measured, because instability in holding the meter to the surface can cause the fault.

10 Claims, 7 Drawing Sheets

FAULT DETECTION AND RESET IN SURFACE REFLECTANCE METER

FIELD OF THE INVENTION

The field of the present invention is surface reflectance meters used for measurements of the reflectance of an opaque surface on a scale relating to distinctness of image. This invention is particularly applicable to portable surface reflectance meters which are held to the surface in question by hand during measuring operations.

BACKGROUND OF THE INVENTION

Surface reflectance meters of the type relating to the present invention are employed in many applications for incoming inspection and quality control. Surface reflectance meters are employed to insure that the appearance of manufactured articles are in accordance with the desired standards. For example, the paint of various body parts of an automobile may be applied at different at different times with differing batches of paint. Unless the quality of the appearance of the body parts can be measured and controlled, the differing body parts will have differing appearances which will not be pleasing to the potential buyer.

The field of the present invention relates primarily to measurements of highly reflective surfaces such as painted or polished metals or ceramics. These opaque surfaces include a predominance of specular reflection rather than diffuse reflection. The present invention is primarily applicable to measurements of distinctness of image. The distinctness of image of a reflection from a surface corresponds to the surface's ability to reflect a sharp image, which is recognizable by an observer. Distinctness of image is rated on a scale of 0 to 100, with 0 being a completely indistinct image and 100 being a completely distinct image.

It is highly desirable to have a portable meter in order to measure this quality of surface reflectance. In particular, a portable instrument which the operator can hold to the surface to be measured by hand could enable rapid incoming inspection or quality control of manufactured parts.

A difficulty exists with portable instruments which are held to the surface by hand. When using such instruments, the stability of the alignment between the instrument and the surface to be measured cannot always be assured. This is in contrast to earlier floor standing instruments which provided a much more stable alignment with the surface to be measured. In portable instruments, such as is the subject of the present invention, a momentary misalignment of the instrument with the surface to be tested can cause the surface reflectance reading to fail. In such an instance it is highly desirable to automatically detect such a reading fault and reset the surface reflectance meter to retake the measurement.

SUMMARY OF THE INVENTION

It is a primary object of the present invention to detect the failure of a surface reflectance measurement due to a failure of the alignment of the surface to be measured and the surface reflectance meter. In accordance with the preferred embodiment of the present invention, the surface reflectance measure is repeated upon such detection of a fault in the original measurement.

In accordance with the preferred embodiment of the present invention, the surface reflectance of the surface to be measured is determined by determining the length of time required for the light intensity reflected from the surface to increase from a first predetermined intensity level to a second predetermined intensity level upon withdrawal of a light chopper from the optical path between a light source, the surface to be measured and a light detector. It is an object of the present invention to provide fault detection and indication of a fault when the light intensity detected by the light detector fails to reach the second predetermined intensity level after a predetermined period of time.

In accordance with the preferred embodiment of the present invention, the surface reflectance meter includes a microprocessor system which is programmed to detect the length of time required for the light intensity to change from the first predetermined intensity to the second predetermined intensity level. It is an object of first embodiment of the fault detection means to determine if the microprocessor system has failed to signal an external device after a predetermined period of time, thereby indicating that the surface reflectance measurement has failed. In accordance with this embodiment of the present invention the microprocessor system is reset after detection of the fault via a nonmaskable interrupt of the microprocessor system. In accordance with a second preferred embodiment of the present invention the fault is detected by a fault detection program which is part of the program of the microprocessor system. This fault detection program determines if a predetermined period of time has elapsed since the light intensity passed the first predetermined intensity level without passing the second predetermined intensity level. Upon detection of such a lapse of time, the fault detection program resets the measurement desired.

It is a further object of the present invention to provide this detection of the failure of the surface reflectance measure in a hand portable measuring instrument which can selectively determine either the distinctness of image of the surface to be tested or the gloss of the surface to be tested.

BRIEF DESCRIPTION OF THE DRAWINGS

These and other objects and aspects of the present invention will be further understood from the following description taken in conjunction with the drawings in which.

DETAILED DESCRIPTION OF THE PREFERRED EMBODIMENTS

Figure 1:
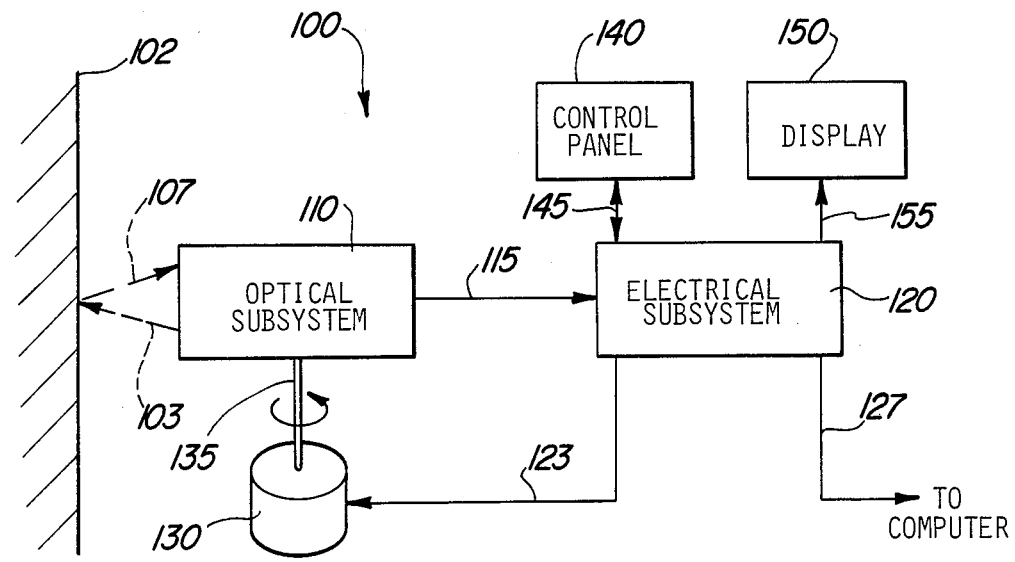
FIG. 1 illustrates a general block diagram of the surface reflectance meter in accordance with the present invention.

FIG. 1 illustrates the general construction of the surface reflectance meter 100. Surface reflectance meter 100 includes optical subsystem 110, electrical subsystem 120, motor 130, control panel 140 and display 150.

Optical subsystem 110 provides the optical interface to the surface 102 to be measured. Optical 110 generates a beam of light 103. This beam of light is reflected from the surface to be measured 102 and returns to the optical subsystem 110 as reflected light 107. Optical subsystem 110 includes some moving parts (not illustrated in FIG. 1) which are driven by motor 130 via motor shaft 135. The optical subsystem measures the reflected light 107 and transmits signals corresponding to this measurement to electrical subsystem 120 via sensor lines 115.

The major control and processing functions of surface reflectance meter 100 are performed by electrical subsystem 120. Electrical subsystem 120 receives signals corresponding to the reflected light from optical subsystem 110 via sensor lines 115. Electrical subsystem 120 controls the operation of motor 130 via motor drive lines 123. Control panel 140 provides the interface between surface reflectance meter 100 and the operator. Control panel 140 is bidirectionally coupled to electrical subsystem 120 via lines 145. The electrical subsystem 120 provides a display on display 150 which is specified by the display drive lines 155. In addition, electrical subsystem 120 can provide a computer output via computer output lines 127.

Figure 2:
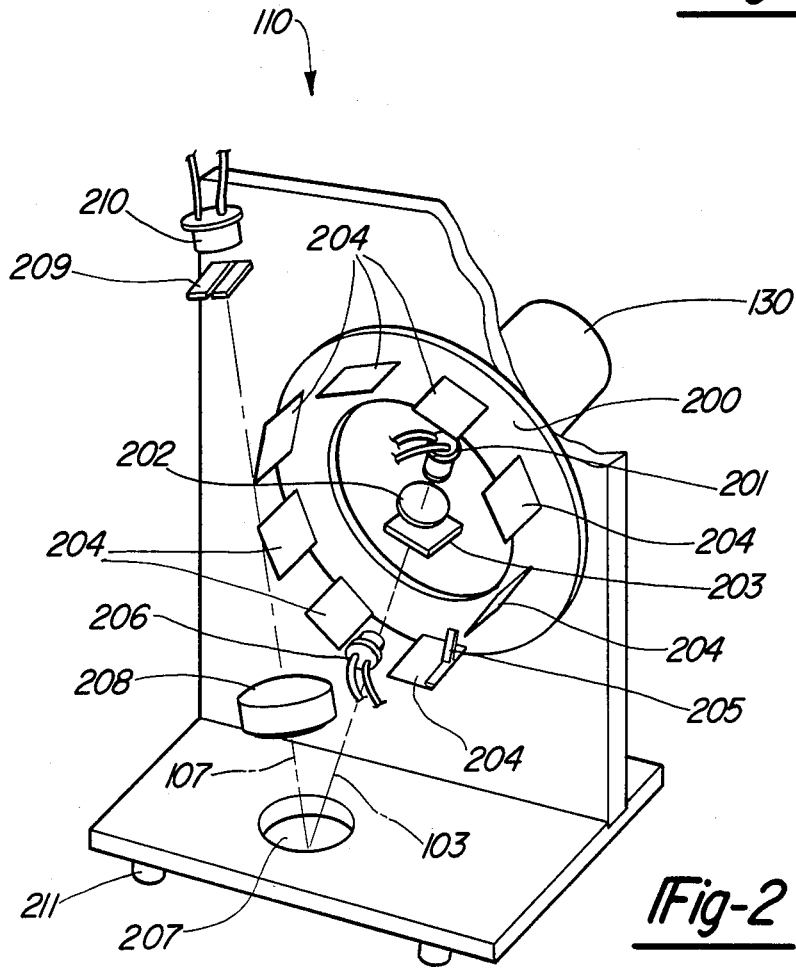
FIG. 2 illustrates components of the optical system of the preferred embodiment of the present invention.

FIG. 2 illustrates the major components of optical subsystem 110. Optical subsystem 110 includes a rotating platter 200 upon which is mounted a plurality of chopper blades 204. The preferred embodiment includes eight such chopper blades 204. These chopper blades are mounted at varying distances from the center of rotation of platter 200. The reason for this variation in distances will be further explained below. Platter 200 is rotated by a motor 130 via motor shaft 135 (not shown). One of the chopper blades 204 includes a synchronization mirror 205. This synchronization mirror 205 is employed in conjunction with photodetector 206 in order to provide a synchronization signal to electrical subsystem 120. The use of this synchronization signal will be more fully disclosed below.

Optical subsystem 110 includes light emitting diode 201 as a light source. Light emitting diode 201 preferably generates infrared light. The light from light emitting diode 201 passes through collimating lens 202 and light diffusor 203. The purpose of collimating lens 202 and diffusor 203 is to provide a focused light spot on the surface to be measured 102.

Light emitting diode 201, collimating lens 204 and diffusor 203 are stationary while platter 200 including chopper blades 204 rotate about light emitting diode 201, collimating lens 204 and diffusor 203 in order to periodically interrupt the light from light emitting diode 201. This light which is periodically interrupted by chopper blades 204 is the light beam 103 produced by optical subsystem 110. This light passes through opening 207 in the outer casing of the surface reflectance meter and returns as reflecting beam 107. In addition, as the platter 200 rotates, the synchronization mirror 205 which is attached to one of the chopper blades 204 periodically reflects the light from light emitting diode 201 to photodetector 206. The output of photodetector 206 is employed for the purpose of synchronizing the interpretation of the received light intensity.

The reflected beam 107 from the surface 102 goes to imaging lens 208. Imaging lens 208 provides a focused image of the light spot appearing on surface 102 at the position of slit 209. Behind slit 209 receiving the light passed therethrough is photodetector 210. Photodetector 210 detects the intensity of the light reflected from the surface 102. This signal is applied to electrical subsystem 124 for interpretation as the surface reflectance measure.

Figure 3:
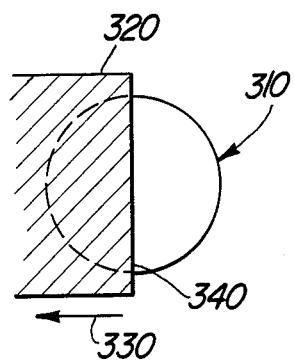
FIG. 3 illustrates the image of the light source and the chopper blade at the surface to be tested.

FIG. 3 illustrates the light image at the surface 102. This light image includes a bright spot 310 corresponding to the diffused light from light emitting diode 201. This image further includes a shadow 320 which is formed by one of the chopper blades 204. This shadow 320 moves in the direction indicated by 330 on account of the rotation of platter 200. This shadow 320 has an edge 340 corresponding to the edge of the chopper blade. A number of shadows 320 from the various chopper blades 204 periodically crosses the bright spot 310 of the image of the light appearing on the surface 102.

Figure 4:
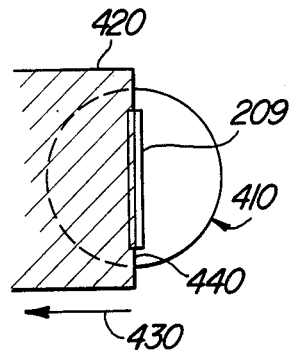
FIG. 4 illustrates the image of the light source and the chopper blade at the slit between the surface and the lights detector.

FIG. 4 illustrates the image at the plane of slit 209. This image includes an image of the bright spot 410 from the light emitting diode 201. The slit 209 is completely contained within this bright spot 410. FIG. 4 further illustrates shadow 420 which passes across slit 204 in the direction indicated by 430. The change in light intensity caused by the passage of the edge 440 of shadow 420 across slit 209 is measured by the surface reflectance meter in order to determine the reading.

In operation the surface reflectance meter 100 is hand held against surface 102 using feet 211 (FIG. 2) to provide a predetermined spacing between the optical system and the surface to be measured. Light rays 103 pass through hole 207 in the outer casing of the meter, are reflected from surface 102 and return through hole 207 as reflected light 107. This reflected light is detected by photodetector 210.

Figure 5:
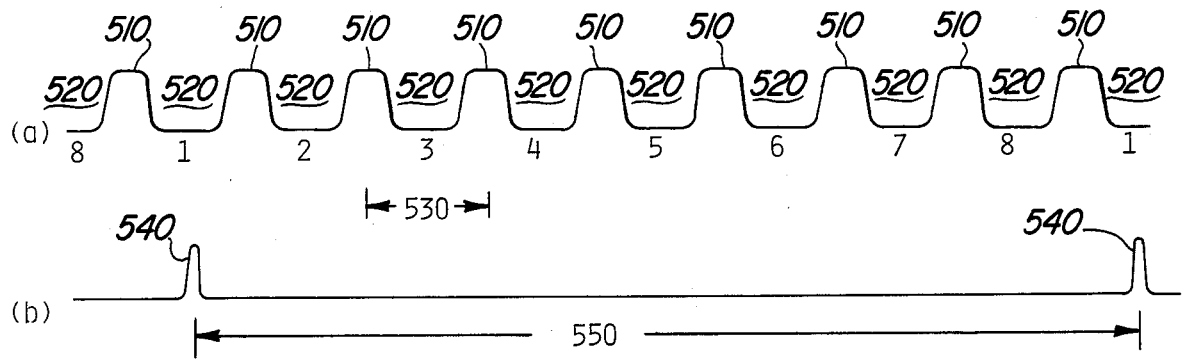
FIGS. 5a, 5b illustrates the light intensity detected by the optical sensor and the synchronization sensor respectively.

FIG. 5 illustrates the typical measured light intensity at photodetector 210 and photdetector 206. FIG. 5(a) illustrates the light intensity detected by photodetector 210. This detected light intensity includes a plurality of light pulses 510 separated by dark regions 520. In the preferred embodiment of the present invention there are eight chopper blades 204. Accordingly, FIG. 5(a) illustrates eight dark intervals 520 corresponding to the shadows produced by the eight chopper blades 204. The time interval 530 between the peaks of light pulses 510 is determined by the spacing of the dark intervals 520. This is in turn determined by the number of chopper blades 204 and the speed of rotation of platter 200.

FIG. 5(b) illustrates the light intensity measured by photodetector 206. Photodetector 206 measures a single short pulse 540 during each rotational period of platter 200. As illustrated in FIG. 5(b) pulse 540 occurs during the dark period 520 caused by chopper blade number 1.

This occurs because synchronization mirror 205 directs light to photodetector 206 during the time in which the first chopper blade is interrupting light beam 103. The interval 550 between successive pulses 540 is solely dependent upon the speed of rotation of platter 200. This time interval gives a measure of the speed of rotation of platter 200.

Figure 6:
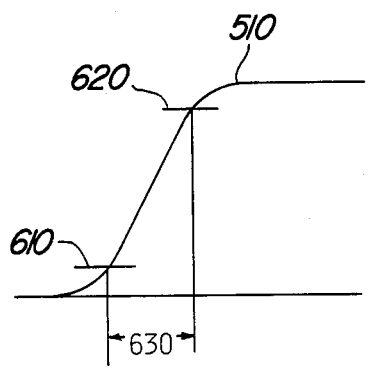
FIG. 6 illustrates the manner of detection of the rise time of the pulses detected by the optical sensor.

FIG. 6 illustrates the leading edge of a typical light pulse 510. This leading edge corresponds to the passage of edge 440 of shadow 420 across the slit 209. This occurs as the edge of the chopper blade 204 is withdrawn from the light path between light emitting diode 201 and photodetector 210. The passage of the edge 440 of shadow 420 across slit 209 causes a rapid increase in the light intensity measured by photodetector 210. This rapid increase is illustrated in FIG. 6. The surface reflectance meter determines the rate of this increase in light intensity by measuring the period of time 630 required for the light intensity of pulse 510 to go from a first predetermined intensity level 610 to a second predetermined intensity level 620. The sharper the reflected image of edge 440 of shadow 420, the shorter is the time interval 630. In addition, the higher the gloss of surface 102 the shorter the time interval 630. In accordance with the preferred embodiment of the present invention, the first predetermined intensity level 610 is approximately $\frac{1}{8}$ of the expected maximum intensity and the second predetermined level 620 is approximately $\frac{7}{8}$ of the maximum expected intensity for measuring the distinctness of image of the surface 102.

A curved surface tends to defocus the image of the edge 440 of shadow 420. This is because a curved surface is not exactly at the desired distance for measurement. As will be recalled, the spacing feet 211 enable the surface reflectance meter 110 to be disposed at a predetermined measurement distance from the surface 102. In the case of a curved surface of the image 310 of light emitting diode 201 is not properly focused on the surface. A convex surface causes the image to focus further from the surface than a flat surface. Conversely, a convex surface causes the image to focus nearer to the surface than a flat surface. Thus, the sharpness of focus of edge 440 appearing at slit 209 would be improper unless this defocusing tendency were corrected. The provision of the eight chopper blades 204 at varying distances from the center of rotation of platter 200 provides this correction. Because chopper blades 204 are disposed at varying distances from the center of rotation of platter 200 and hence varying distances from the surface 102, a range of focal points is provided. The distances of chopper blades 204 from the center of rotation of platter 200 are selected in order to provide a range of focal distances covering the expected range of curved surfaces to be measured. The most sharply focused image will have the fastest rise time 630, therefore the surface reflectance measure is taken from the light pulse 510 having the shortest rise time interval 630.

Figure 7:
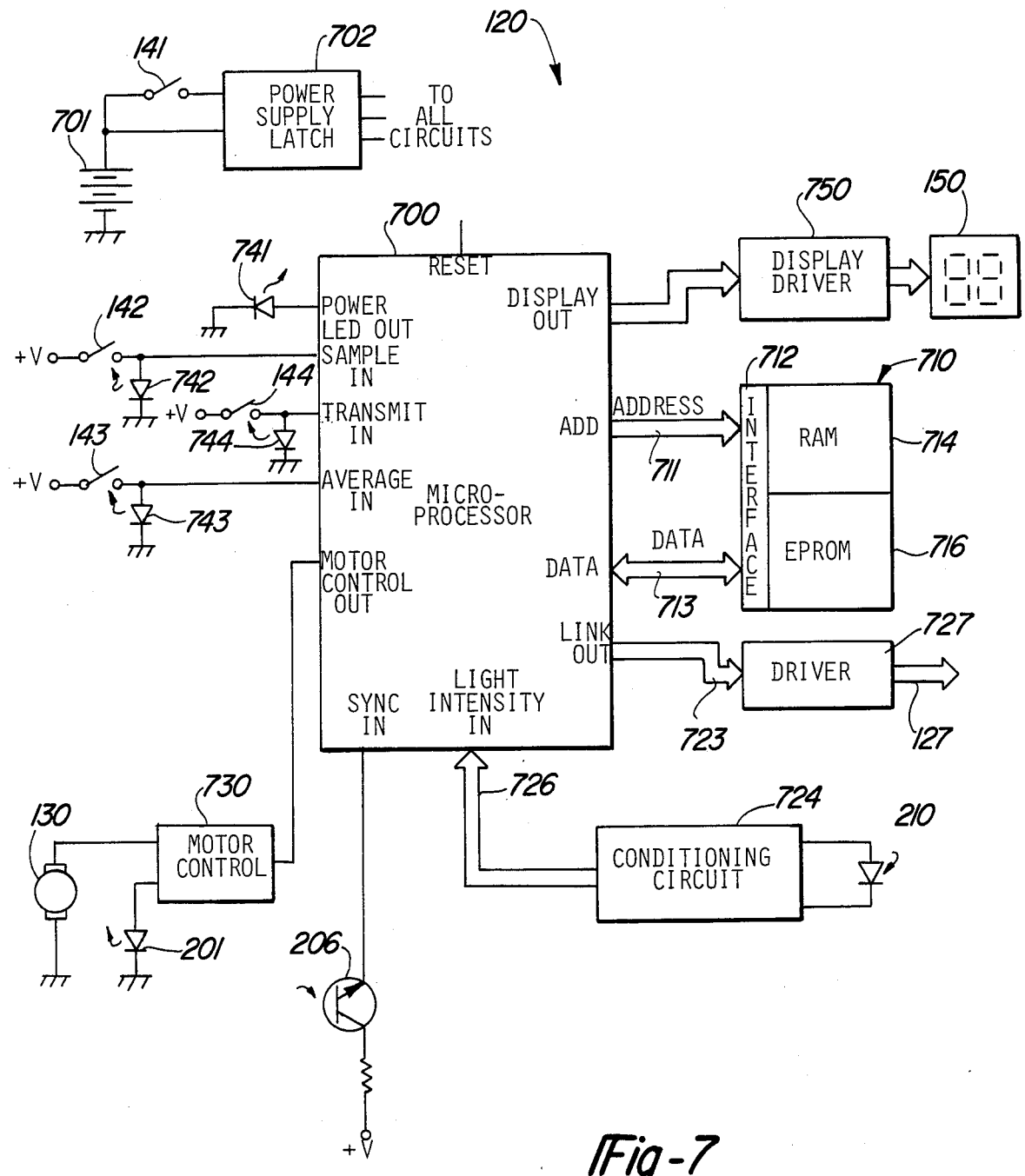
FIG. 7 illustrates in semi-block diagram form the electrical subsystem.

FIG. 7 illustrates the major parts of electrical subsystem 120. Electrical subsystem 120 includes microprocessor 700, memory system 710, and numerous peripheral circuits. In the preferred embodiment microprocessor 700 is a Motorola 146805.

The application of electric power of electrical subsystem 120 is controlled by momentary contact pushbutton power switch 141. Momentary contact pushbutton power switch 140 is a part of control panel 140. Battery 701 is connected to power supply latch 702 and to one terminal of power switch 141. The other terminal of power switch 141 is connected to power supply latch 702. Momentary depression of power switch 141 causes power supply latch 702 to couple electric power from battery 701 to the various circuits of electrical subsystem 120. A further depression of power switch 141 toggles power supply latch 702 to withdraw power from circuits of electrical subsystem 120.

The major and control processing functions of electrical subsystem 120 are performed by microprocessor 700. Microprocessor 700 is connected to memory system 710 which includes interface 712, random access memory 714, and electrically programmable read only memory 716. Microprocessor 700 provides addresses to interface 712 by an address bus 711. This address applied to address bus 711 supplies selection of the proper memory word within memory system 710 accessed by microprocessor 700. In the preferred embodiment, a single address space covers both random accessed memory 714 and electrically programmable read only memory 716. In the preferred embodiment both random access memory 714 and electrically programmable read only memory 716 contain 2K bytes of memory.

These two memory areas are employed differently. Random access memory 714 is employed to store temporary values used in the operation of microprocessor 700. These temporary values include intermediate calculated results which are stored prior to use, the value of the reflectance measure of the last sample, and the average reflectance measure and sample size when operating in the average mode. Electrically programmable read only memory 716 stores permanent values such as the control program for microprocessor 700 and the look up table for the measurement process. It would be understood by those skilled in the art that electrically programmable read only memory 716 could be replaced by a read only memory if enough surface reflectance meters are constructed at one time to justify the production of read only memories.

Data is bidirectionally coupled between microprocessor 700 and memory system 710 by a data bus 713. Data bus 713 is connected to interface 712 and exchanges data between microprocessor 700 and memory system 710 at the address specified by address bus 711.

As will be further illustrated below, microprocessor 700 periodically provides an output signal to power light emitting diode 741, which is a part of control panel 140, to provide an indication of the operation of electrical subsystem 120.

Microprocessor system 700 is responsive to sample switch 142, average switch 143, and transmit switch 144 to control various functions of the electrical subsystem 120. Each of these switches are preferably of the momentary contact push button type. Momentary actuation of sample switch 142 causes a signal to be applied to the sample input of microprocessor 700. Actuation of sample switch 142 further provides illumination of light emitting diode 742. Light emitting diode 742 is a part of control panel 140. Illumination of light emitting diode 742 indicates the request for a sample to be taken by the surface reflectance meter 100.

In a similar fashion, momentary actuation of average switch 143 provides a signal to the average input of microprocessor 700 and momentarily actuates light emitting diode 743. This momentary actuation of light emitting diode 743 indicates the toggling of the average mode.

In a similar fashion, momentary actuation of transmit switch 144 provides a signal to the transmit input of microprocessor 700 and actuates light emitting diode 744. This serves to request transmission of data to an external computer via lines 127. Illumination of light emitting diode 744, which is a part of control panel 140, indicates actuation of transmit switch 144. Upon reception of such a request, microprocessor 700 provides an output computer link signal on bus 723 to driver circuit 727. Driver circuit 727 provides the computer link output on bus 127.

Microprocessor 700 includes a motor control output applied to motor control circuit 730. Responsive to the motor control output signal from microprocessor 700, motor control circuit 730 provides the proper power to motor 130 for driving motor 130 at the desired speed. Motor control 730 is further connected to light emitting diode 201 for applying the desired power to this element.

Microprocessor 700 receives signals from photodetector 206 and photodetector 210. Photodetector 206 is illustrated as a photo transistor whose output signal is applied to a synchronization input of microprocessor 700. As you will remember from FIG. 5, the output of photodetector 206 is a short pulse 540 which occurs once each rotation of platter 200. This syncronization signal is used to provide timing control for the operation of microprocessor 700.

FIG. 7 illustrates photodetector 210 as a photodiode. This photodiode is connected to conditioning circuit 724 which is further connected to a light intensity input of microprocessor 700 via bus 726. In the preferred embodiment, conditioning circuit 724 provides analog to digital conversion of the signal from photodetector 210, for processing by microprocessor 700.

A display output bus of microprocessor 700 is connected to display driver circuit 750. Display driver circuit 750 provides proper output for display 150. In the preferred embodiment, display 150 is a pair of seven segment liquid crystal display digits. Microprocessor 700 is programmed to provide the proper signals to display driver 750 to display the measured surface reflectance via display 150.

Microprocessor 700 is illustrated as including a reset input. This reset input of the microprocessor 700 corresponds to a non-maskable interrupt pin. This non-maskable interrupt pin is employed in one of the embodiments of the present invention in a manner which will be further illustrated below.

Those skilled in the art of designing microprocessor systems would realize that the circuits illustrated in FIG. 7 are conventional. That is, construction of the microprocessor system illustrated in FIG. 7 would be within the capability of one of ordinary skill in this art. In addition, those skilled in the art would understand that the operation of microprocessor 700 is dependent upon the particular control program stored wiithn electrically programmable read only memory 716. Microprocessor 700 can perform a variety of tasks in response to the control program FIGS. 8 and 9 a-c illustrate a flow chart of the program stored within electrically programmable read only memory 716 in accordance with the preferred embodiment of the present invention. These flow charts show the general overall steps performed by microprocessor 700. Upon selection of the microprocessor to embody microprocessor 700, those skilled in the art of microprocessor systems would be able to construct a program in accordance with these flow charts to control microprocessor 700.

Program 800 illustrates the overall top level program employed for control of microprocessor 700 in accordance with the preferred embodiment of the present invention. Program 800 is a continuously repeated loop which generally causes microprocessor 700 to detect the condition of momentary contact pushbutton switches 142, 143, and 144.

The loop of program 800 is begun by strobing the power light emitting diode (processing block 801). In accordance with the present invention, microprocessor 700 periodically turns on light emitting diode 741 for a predetermined period of time during each loop of the program 800. This provides a flashing of a light emitting diode 741 which indicates the operation of surface reflectance meter 100.

Next, program 800 tests to determine whether or not the average switch 143 has been depressed (decision block 802). If this average switch has been depressed program 800 tests to determine whether or not program 800 is in the average mode (decision block 803). If the program 800 is not in the average mode then the average mode is set (processing block 804). On the other hand, if the program 800 is in the average mode, then this average mode is reset (processing block 805) thereby cancelling the average mode. Regardless of the outcome of this process program 800 proceeds to decision block 806.

Decision block 806 detects whether or not the sample switch 142 has been depressed. If the sample switch has been depressed then program 800 takes a sample of the reflectance characteristics of the surface 102 (processing block 807). The details of this process is further illustrated in FIGS. 9a to 9c. If the sample switch was not depressed or if the sample switch was depressed and a sample has been taken then process control passes to decision block 808.

Program 800 next test determines whether or not transmit switch 144 has been depressed (decision block 808). If the transmit switch has been depressed then program 800 tests to determine whether or not the system is in the average mode (decision block 809). In the event that program 800 is in the average mode then the average reading is transmitted (processing block 810). If, on the other hand, the average mode has not been set then program 800 transmits the latest sample data (processing block 811). Regardless of which of these cases is true, the program 800 returns to processing block 801 to repeat the cycle.

Figure 8:
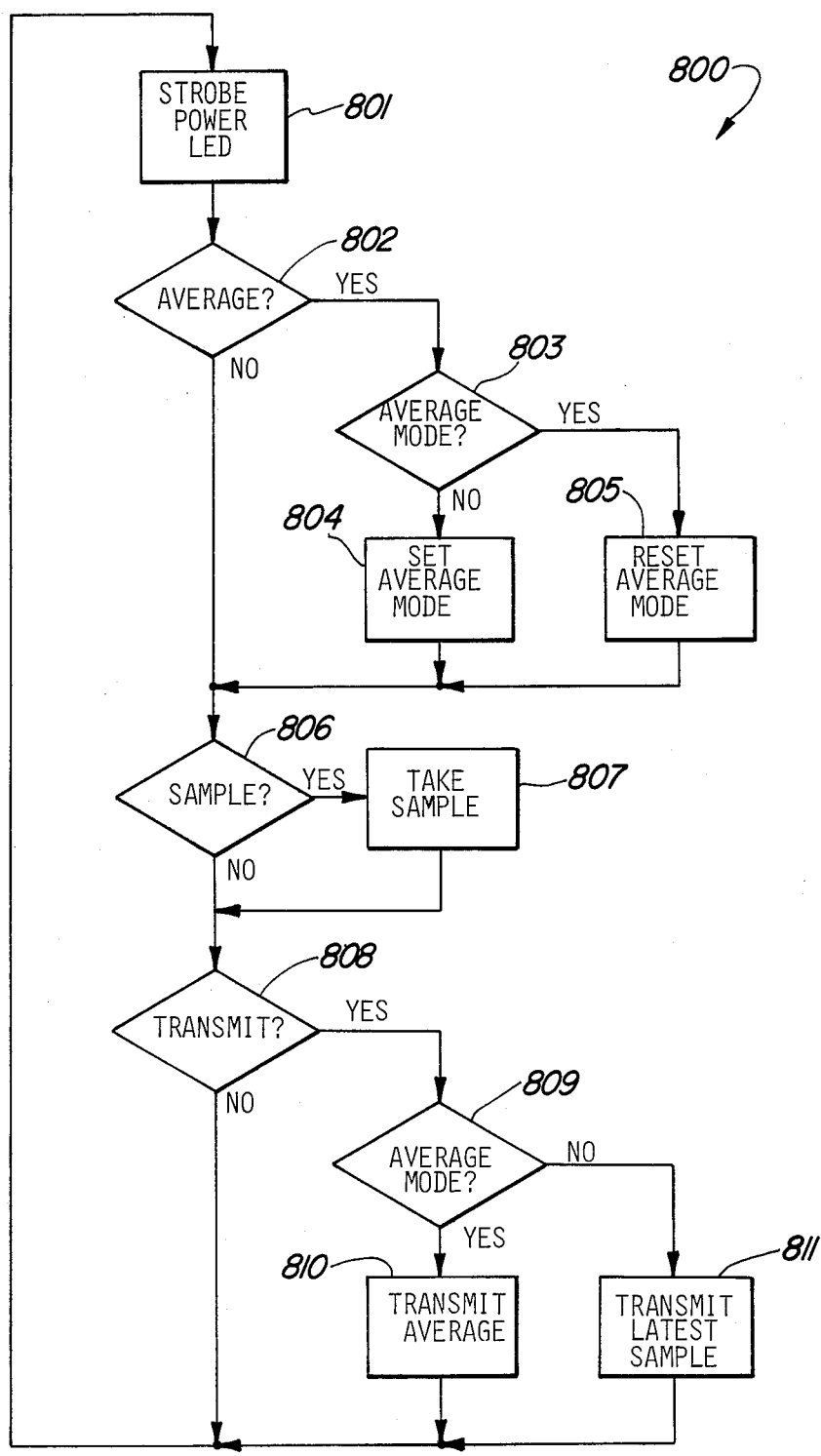
FIG. 8 illustrates the preferred embodiment of the general program of the microprocessor of the electrical system.
Figure 9:
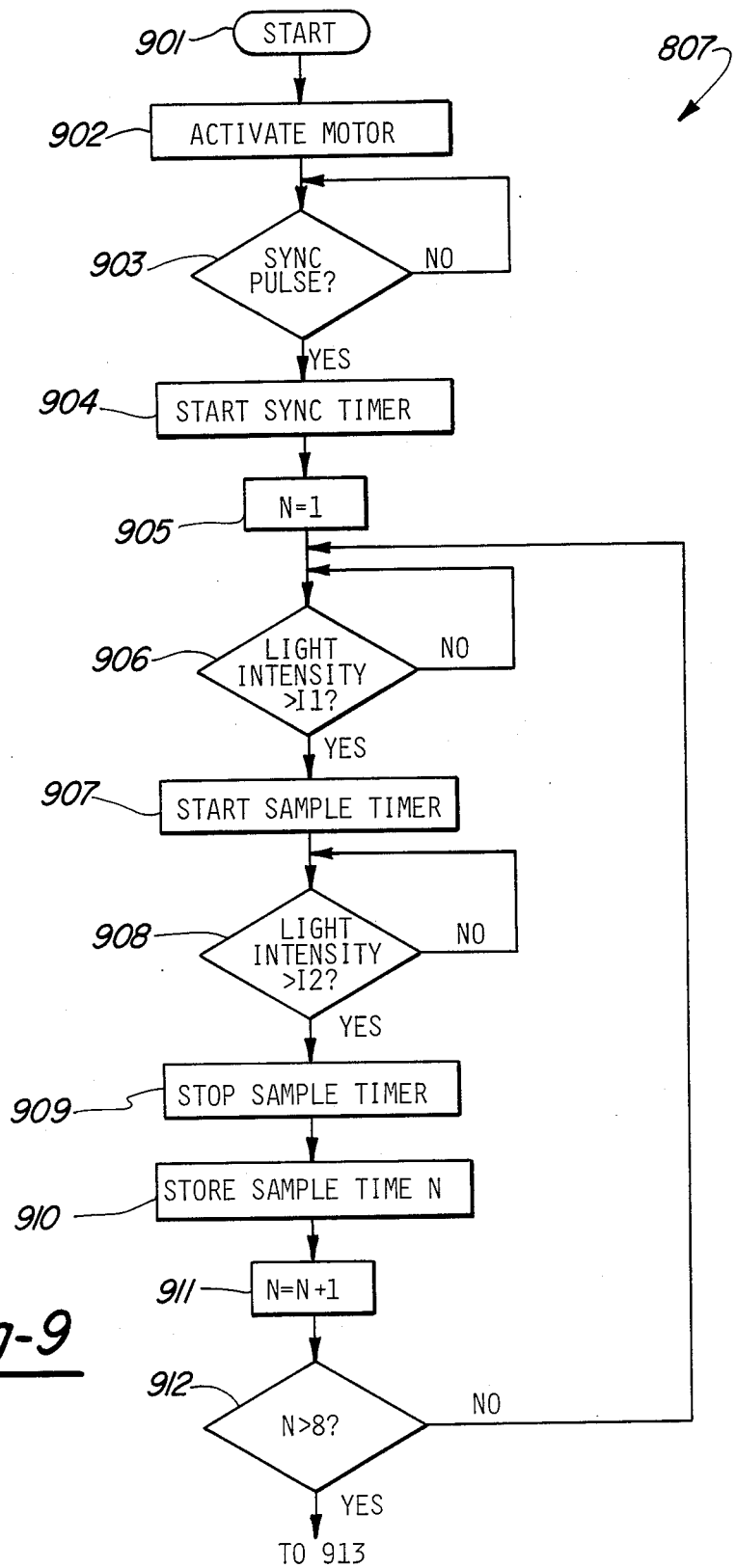
FIGS. 9a, 9b and 9c together illustrate the preferred embodiment of the sampling program of the microprocessor system of the electrical subsystem.
Figure 9A:
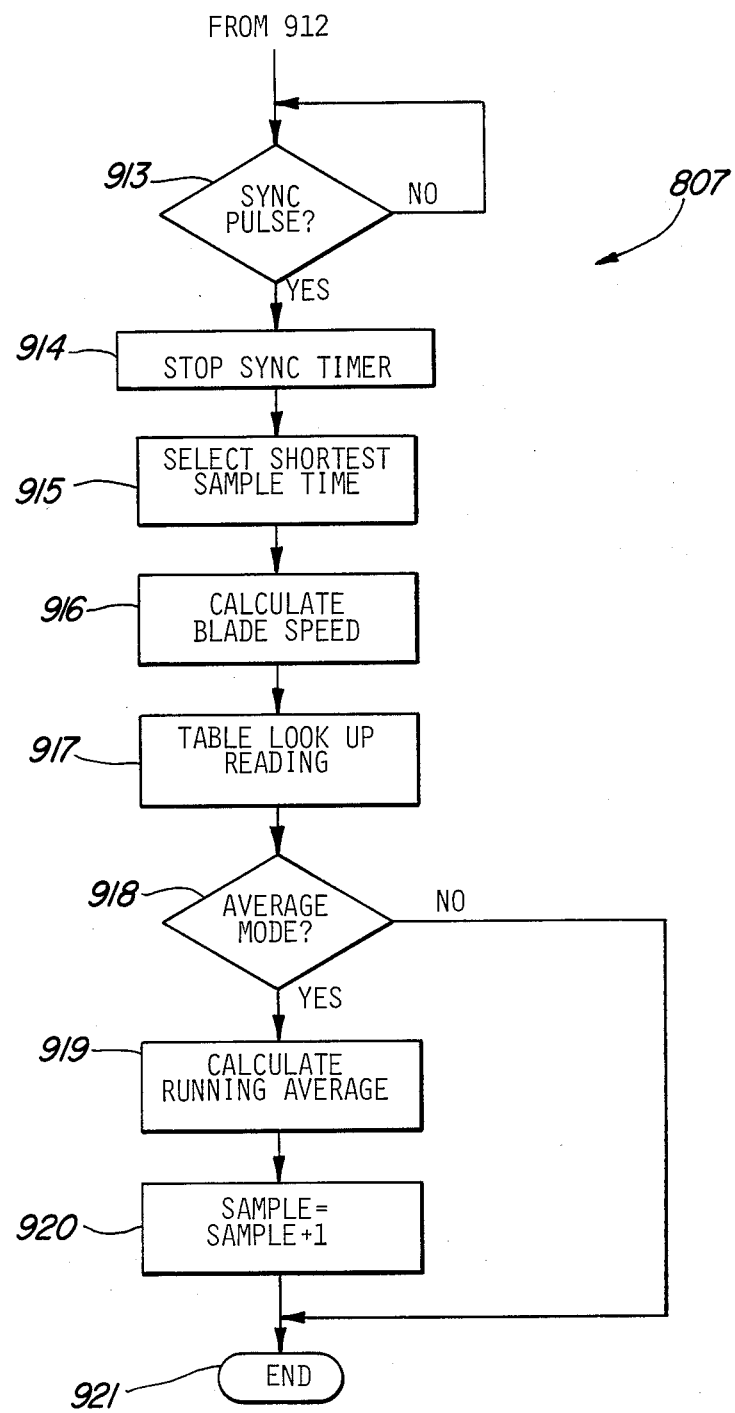

FIGS. 9a, 9b, and 9c together illustrate processing block 807, the process for taking a sample measurement. This program begins at start block 901 which is entered from decision block 806 illustrated in FIG. 8. Firstly, program 807 activates the motor (processing block 902). This involves providing the necessary motor control signal to motor control circuit 730 in order to start motor 130 and drive it to the desired speed.

Program 807 next tests to determine whether a synchronization pulse has been received (decision block 903). As the synchronization mirror 205 passes through the light rays 103, a pulse 540 appears as the output of photodetector 206. This is applied to the synchronization input of microprocessor 700. If such a synchronization pulse is not detected then program 800 repeats the execution of decision block 903. This process continues until the synchronization pulse has been received. Thereupon, process control passes to processing block 904.

Program 807 next starts a synchronization timer (processing block 904). This process captures the current time and enables the time 550 between consecutive synchronization pulse 540 to be determined.

Program 807 next sets a counter equal to one (processing block 905). This counter will enable distinctions to be made between the rise times corresponding to each of the eight chopper blades 204.

Program 807 next checks to determine whether the light intensity is greater than the first predetermined intensity level I1 (decision block 906). In the event that the light intensity is not greater than this first predetermined intensity level, then the test is repeated until the light intensity exceeds this first predetermined level. Upon detection of this event a sample timer is started (processing block 907). This sample timer will be used in order to determine the interval 630 during which time the light intensity increases between the first predetermined intensity level and the second predetermined intensity level.

Program 807 next tests to determine whether the light intensity has exceeded the second predetermined intensity level I2 (decision block 908). In the event that the light intensity has not exceeded this second predetermined intensity level, decision block 908 is repeated until this event is detected. Upon detection of this event the sample timer is stopped (processing block 909). This sample time is then stored as a sample time N (processing block 910). Note that the number N will be changed in this loop in accordance with the number of light chopper blades which have been previously detected. Therefore, a number of such sample times will be collected.

Next program 807 increments the sample number N (processing block 911) and checks to determine whether or not this number exceeds eight (decision block 912). This number eight corresponds to the number of light chopper blades. In the event that this sample number is not greater than eight then the process returns to decision block 906. This enables detection of the interval 630 required for the light intensity to pass between the first and second predetermined intensity levels for the next light pulse 510. If however the sample number exceeds eight, the number of light chopper blades in the preferred embodiment, then process control passes to decision block 913.

Program 807 next tests to determine whether or not a synchronization pulse is received (decision block 913). This detection of a synchronization pulse is the same as that previously illustrated at decision block 903. In the event that a synchronization pulse is not detected then this step is repeated. However, if the synchronization pulse has been detected then the synchronization timer is stopped (processing block 914). The time now held in the synchronization timer indicates the interval 550 between consecutive synchronization pulses. This interval will be later employed as a measure of the speed of the light chopper blades.

Program 807 next selects the shortest sample time previously taken (processing block 915). As noted above, if the surface to be measured is curved in some way then the image of the edge 440 of the shadow of the light chopper blade 420 may be blurred. As a consequence a plurality of chopper blades 204 are provided at varying distances from the center of plate 200. This varying distance enables the spot 310 to be focused at a range of possible locations of the surface 102. As previously discussed above, the shortest rise time corresponds to the light chopper blade with the best focus at the plane of slit 209. Therefore, the surface reflectance meter 100 is designed to select the shortest rise time to provide the best measure of the reflectivity of the surface.

Program 807 next calculates the blade speed (processing block 916). This calculation is made from the time on the synchronization timer, that is the time 550 between consecutive synchronization pulses 540. Due to variation in the charge state of battery 701 which provides the power for motor 130, it is expected that the rate of rotation of plate 200, and hence the blade speed, may vary slightly. In addition, the sample number of the shortest sample time is also required to make this calculation. The sample number corresponds to the individual light chopper blade 204 which enabled the rise time measurement. Because these light chopper blades are mounted at different real distances from the center of rotation of plate 200, their speed of motion through light ray 103 differs even assuming a constant rotational speed.

The relationship between the shortest measured rise time, taking into account the blade speed, is expected to be non-linear in relationship to the scale of the reflectivity measure to be indicated. Therefore, the reflectivity measure is found by a table look up operation (processing block 917). That is, knowing the rise time and the blade speed a particular reading within a look up table stored within electrically programmable read only memory 716 is recalled. Processing block 917 may include suitable interpolation between adjacent entries in the lookup table if desired.

Program 807 next tests to determine whether or not the program is in average mode (decision block 918). In the event that the apparatus is not in average mode then program 807 is finished and is exited by an exit block 921. If the apparatus is in average mode then a calculation is made of the running average (processing block 918). Next, the number of samples in the running average is incremented (processing block 920). After this calculation the program 807 is complete and is exited by an exit block 921.

Figure 10:
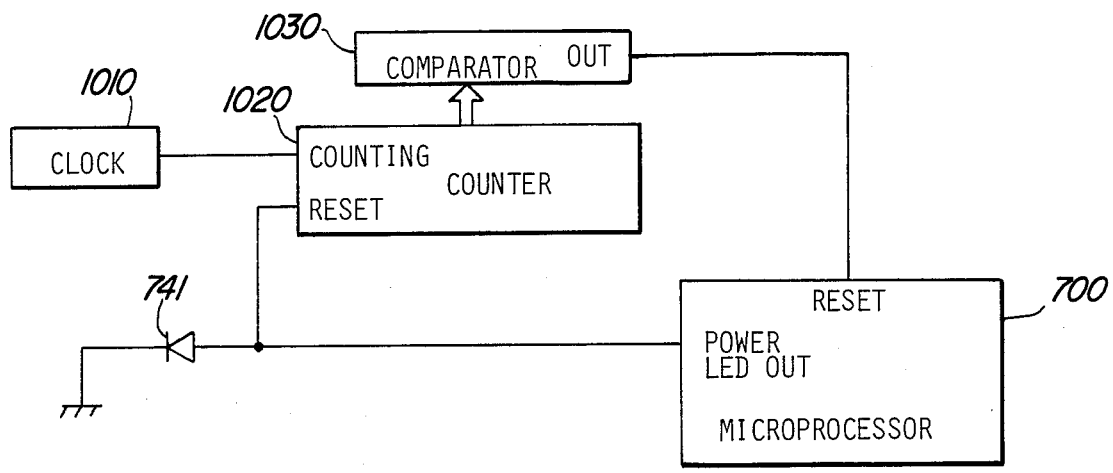
FIG. 10 illustrates the fault detection and reset circuits in accordance with a first embodiment of the present invention.

FIG. 10 illustrates hardware employed in conjunction with microprocessor 700 and the program 807 illustrated in FIGS. 9a, 9b, and 9c to detect the fault condition and to reset the apparatus. As will be remembered from the above discussion, a momentary instability in the position of optical system 110 in relation to the surface to be tested 102 may result in an improper measure of the reflectance characteristic measure. In particular, it has been found that in a number of instances the light intensity is detected to exceed the first predetermined light intensity level I1 but not to exceed the second predetermined light intensity level I2. In such an event, program 807 remains in a endless loop continuously repeating decision block 908. Without some means of resetting microprocessor 700, this particular part of program 807 will be continuously repeated. The hardware illustrated in FIG. 10 prevents this endless loop condition.

As will be remembered from FIG. 8, program 800 requires periodic strobing of the power light emitting diode (processing block 801). This strobing is provided by a power LED output from microprocessor 700. This output is also applied to the reset input of a counter 1020. Clock 1010 drives the counting input of counter 1020. The count of counter 1020 is continuously compared to a predetermined count by a comparator 1030.

The frequency of clock 1010 and the predetermined number of comparator 1030 are selected to provide a suitable interval via counter 1020 to insure no interruption of normal processes of microprocessor 700, while generating an indication of the abnormal endless loop case. Comparator 1030 generates an output which is supplied to the reset input of microprocessor 700 when the count of counter 1020 exceeds its predetermined count. The reset input of microprocessor 700 is preferably a non-maskable interrupt which causes the processes controlled by microprocessor 700 to be reset as in the case of initial application of electric power to microprocessor 700. This process serves to prevent microprocessor 700 from remaining in the endless loop condition described.

Figure 11:
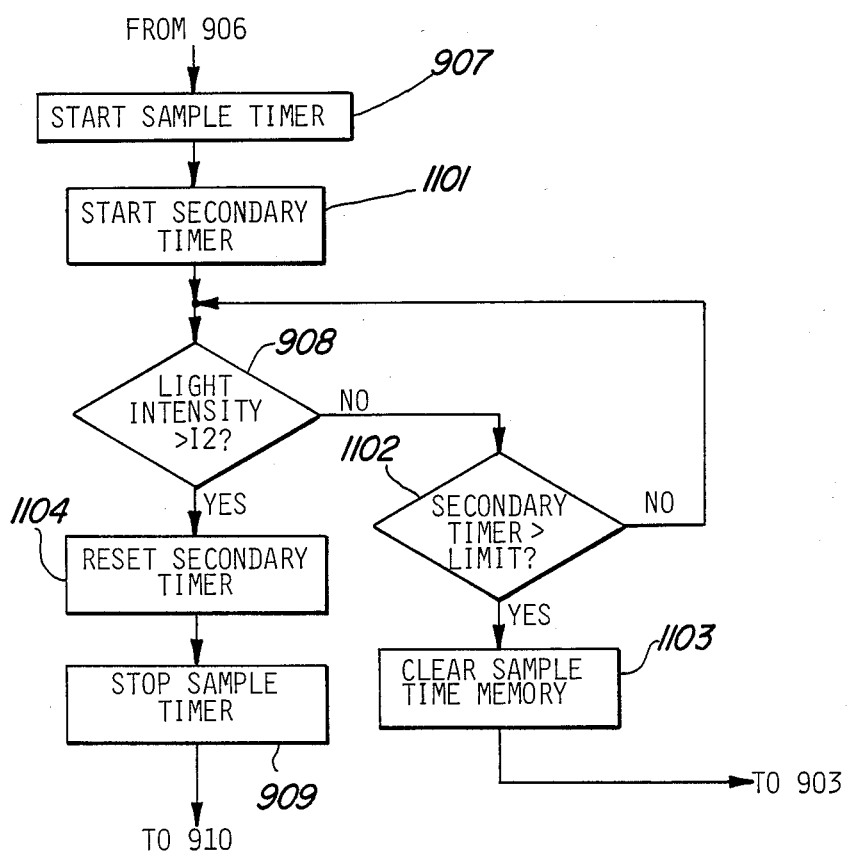
FIG. 11 illustrates the fault detection and reset program in accordance with a second embodiment of the present invention.

FIG. 11 illustrates a modified portion of program 807 in accordance with a second embodiment of the present invention. This modified program 807 also detects and resets the measurement operation when the fault condition noted above is detected.

The modified portion of program 807 is entered from decision block 906. First, the sample timer is started (processing block 907). This process is the same as described above. Next, a secondary timer is also started (processing block 1101). The secondary timer is an addition over the program 807 illustrated in FIGS. 9a, 9b and 9c.

As previously illustrated, the light intensity is tested to determine whether or not it is greater than the second predetermined intensity level I2 (decision block 908). In the event that the light intensity level has not exceeded the second predetermined light intensity level I2, then the program tests to determine whether the time indicated by the secondary timer exceeds a predetermined limit (decision block 1102). This limit is selected in order to permit the light intensity level to reach the second predetermined light intensity level I2 for all normal cases. If this is still a normal case in which the secondary timer does not exceed this limit, then processor control returns to decision block 908 to test whether or not the light intensity level is greater than the second predetermined light intensity level (decision 908). However, in the event that the secondary timer has exceeded the predetermined limit, then a fault condition is detected. In this event, the sample time memory is completely cleared (processing block 1103). This serves to cancel the previously measured and stored sample times for other light chopper blades, if any previous measurements have been made. The process then passes to decision block 903 which detects whether or not a synchronization pulse had been received. Return of control to this portion of the program serves to restart the process of finding the best sample corresponding to the light chopper blade which provides the best focus.

In the event that the light intensity level has exceeded the second predetermined light intensity level I2 prior to the secondary timer exceeding the predetermined time limit, then the secondary timer is reset (processing block 1104). At this time the sample timer is stopped (processing block 909) in the manner previously described. Control of the program then passes to processing block 910 in accordance with the description provided above in reference to FIGS. 9a, 9b and 9c.

The provision of the secondary timer enables the program 807 to test whether or not a reasonable interval has past for detection of the increase of the light intensity level to greater than the second predetermined light intensity level I2. This limit time is preferably set greater then the time required under all foreseeable conditions, in order to prevent false alarms. An advantage of the embodiment illustrated in FIG. 11 over the embodiment illustrated in FIG. 10 is that this limit can be set closer to the optimal limit for that particular process, that is the length of time required for the light intensity level to increase to greater than the second predetermined light intensity level I2. The time set via clock 1010, counter 1020 and comparator 1030, must be somewhat greater in order to provide for delays possible in other portions of program 800. In addition, it is possible to provide a restart of the sampling process without wiping out the previously calculated average and number of samples. This is because the modified portion of program 807 illustrated in FIG. 11 does not completely reset microprocessor 700. On the contrary, the embodiment illustrated in FIG. 10 destroys all information stored by microprocessor 700 and returns to an initialization stage.

We claim:

1. In a surface reflectance meter having a light source, a first optical system for directing light from the light source to a surface to be tested, a light detector means for detecting light intensity, a second optical system for directing light reflected from the surface to be tested to the light detector means, a light chopper means adapted to be interposed and then withdrawn from between the light source and the light detector means, and a flux rate detecting means connected to the light detector means for detecting a first intensity of reflected light and a second intensity of reflected light and measuring the interval therebetween so as to determine the rate of light intensity increase at the light detector means as the light chopper means is withdrawn from between the light source and the light detector means, the improvement comprising:
   a fault detection means connected to said flux rate detecting means for determining if the interval being measured by the flux rate detecting means exceeds a predetermined limit indicative of a fault in the flux rate detecting means that would prevent a proper measure of the rate of light intensity increase.

2. The surface reflectance meter as claimed in claim 1, further comprising:
   a reset means connected to the flux rate detecting means and said fault detection means for causing the surface reflectance meter to repeat a measurement by repeating detection of the rate of light intensity increase upon indication of a fault by said fault detection means.

3. The surface reflectance meter as claimed in claim 1, wherein:
   the flux rate detecting means detects the rate of light intensity increase by determining the length of time required for the light intensity detected by the light detector means to change from a first predetermined intensity level to a second predetermined intensity level higher than said first predetermined intensity level; and
   said fault detecting means detects and indicates a fault when said light intensity detected by said light detector means fails to reach said second predetermined intensity level in a predetermined period of time.

4. The surface reflectance meter as claimed in claim 1, further comprising:

an interpretation means connected to said flux rate detecting means for converting said detected rate of light intensity increase into an indication of distinctness of image according to a predetermined distinctness of image scale.

5. A surface reflectance meter comprising:

a light source;

a first optical system for focusing said light source onto a surface to be tested;

a light chopper means including at least one light chopper blade, said at least one light chopper blade periodically interposed and withdrawn from between said light source and the surface to be tested thereby causing a shadow of the edge of the blade to appear at the surface to be tested;

a light detector means for detecting light intensity;

a second optical system for directing light reflected from the surface to be tested to said light detector means, said second optical system including a narrow slot disposed between the surface to be tested and said light detector means, said narrow slot oriented in parallel with the shadow of the edge of the blade;

a flux rate detecting means connected to said light detector means for detecting the length of time required for the light intensity detected by said light detecting means to change from a first predetermined intensity level to a second predetermined intensity level higher than said first predetermined intensity level as the shadow of the edge of the blade is withdrawn from said narrow slot; and a fault detection means connected to said flux rate detecting means for detecting and indicating a fault when said light intensity detected by said light detecting means fails to reach said second predetermined intensity level in a predetermined period of time.

6. The surface reflectance meter as claimed in claim 5, further comprising:

a microprocessor system having a control program including a flux rate detecting program for detecting the length of time for the light intensity to change from said first predetermined intensity level to said second predetermined intensity level, whereby said flux rate detecting program as implemented by the microprocessor provides said flux rate detecting means.

7. The surface reflectance meter as claimed in claim 6, wherein:

said microprocessor system further includes a lookup table relating the time for the light intensity to change from said first predetermined intensity level to said second predetermined intensity level to an indication of distinctness of image according to a predetermined distinctness of image scale; and said control program further includes an interpretation program for generating an indication of distinctness of image according to said predetermined scale by recalling the indication of distinctness of image corresponding to said detected time for the light intensity to change between said first predetermined intensity level to said second predetermined intensity level.

8. The surface reflectance meter as claimed in claim 7, wherein:

said first predetermined intensity level is approximately one eigth of the expected maximum light intensity reflected from the surface; and said second predetermined intensity level is approximately seven eighths of the expected maximum light intensity reflected from the surface.

9. The surface reflectance meter as claimed in claim 6, wherein:

said control program of said microprocessor system is further adapted to regularly signal a light source; and said fault detection means is connected to said microprocessor system and said light source so as to reset said microprocessor system if said microprocessor system fails to signal said light source after said predetermined period of time.

10. The surface reflectance meter as claimed in claim 6, wherein:

said control program further includes a fault detection program whereby said fault detection program as implemented by the control program of the microprocessor provides said fault detection means and functions to restart a measurement of flux rate if said predetermined period of time has elapsed since said light intensity has passed said first predetermined intensity level without passing said second predetermined intensity level.

* * * * *

UNITED STATES PATENT AND TRADEMARK OFFICE
CERTIFICATE OF CORRECTION

PATENT NO. : 4,761,676

DATED : August 2, 1988

INVENTOR(S) : Wiles et al

It is certified that error appears in the above-identified patent and that said Letters Patent is hereby corrected as shown below:

Column 5, line 27, "1/2" should be --1/8--.

Signed and Sealed this

Twenty-fourth Day of January, 1989

Attest:

DONALD J. QUIGG

Attesting Officer

Commissioner of Patents and Trademarks